United States Patent [19]

Dürckheimer

[11] Patent Number: 4,624,948
[45] Date of Patent: Nov. 25, 1986

[54] CRYSTALLINE MODIFICATION OF CEFTAZIDIM

[75] Inventor: Walter Dürckheimer, Hattersheim am Main, Fed. Rep. of Germany

[73] Assignee: Hoechst Aktiengesellschaft, Fed. Rep. of Germany

[21] Appl. No.: 600,773

[22] Filed: Apr. 16, 1984

[30] Foreign Application Priority Data

Apr. 16, 1983 [DE] Fed. Rep. of Germany ....... 3313818

[51] Int. Cl.$^4$ ................. C07D 499/44; A61K 31/545
[52] U.S. Cl. .................................. 514/206; 514/203; 540/225
[58] Field of Search .......................... 544/25; 424/246; 514/203, 206

[56] References Cited

U.S. PATENT DOCUMENTS 4,258,041 3/1981 O'Callaghan et al. ................. 544/22
4,329,453 5/1982 Brodie et al. .......................... 544/25
4,537,959 8/1985 Chou ..................................... 544/25

FOREIGN PATENT DOCUMENTS 3313818 10/1984 Fed. Rep. of Germany .
2466467 10/1980 France .
2466469 10/1980 France .
2025398 1/1980 United Kingdom .

Primary Examiner—Nicholas S. Rizzo
Attorney, Agent, or Firm—Finnegan, Henderson, Farabow, Garrett & Dunner

[57] ABSTRACT

Anhydrous crystalline (6R,7R)-7-[(Z)-2-(2-aminothiazol-4-yl)-2-(2-carboxyprop-2-oximino)acetamido]-3-(1-pyridiniummethyl)-3-cephem-4-carboxylate and a process for its preparation, a pharmaceutical formulation which is active against bacterial infections and contains this compound and a process for the preparation of the formulation and the use of this compound for controlling bacterial infections.

3 Claims, No Drawings

CRYSTALLINE MODIFICATION OF CEFTAZIDIM (6R, 7R)-7-[(Z)-2-(2-Aminothiazol-4-yl)-2-(2-carboxyprop-2-oximino)acetamido]-3-(1-pyridiniummethyl)-3-cephem-4-carboxylate (ceftazidim) is a cephalosporin antibiotic of the 3rd generation which has pronounced efficacy for Gram-negative pathogens, including pseudomonas species (cf. German Offenlegungsschrift No. 2,921,316). The pentahydrate of this compound (cf. German Offenlegungsschrift No. 3,037,102) has hitherto been the only crystalline form which is well suited for parenteral use.

It is known that the stability of cephalosporins is limited and that they readily decompose on storage. The cause of this is the high sensitivity to hydrolysis of the $\beta$-lactam ring which can even react slowly with water bound in the crystal lattice when the molecule is exposed to heat stress or is stored for a prolonged period at room temperature. Thus it is very important to employ the most stable crystalline form possible for medical use of a cephalosporin antibiotic.

It has now been found that ceftazidim can be converted into a new crystalline modification which is distinguished from the pentahydrate by increased stability to heat and is particularly well suited for a parenteral formulation.

Thus the invention relates to an anhydrous crystalline ceftazidim, its pharmaceutical formulations, and a process for its preparation, which comprises dehydrating a crystalline ceftazidim hydrate, preferably the pentahydrate, to constant weight. The term "anhydrous" does not rule out a small content of water as long as it does not alter the indicated physical properties.

The crystalline modification according to the invention has a characteristic Debye-Scherrer diagram (Table 1) which proves the presence of a new crystalline form having new physical and chemical properties.

Any crystalline ceftazidim hydrate, for example one containing 1.5 mol of water (cf. German Patent Application No. 3,313,816.8 filed Apr. 16, 1983), preferably the pentahydrate (German Offenlegungsschrift No. 3,037,102), is suitable as the starting material.

The dehydrating agents which may be used are the substances customarily used for this in the laboratory, such as, for example, phosphorus pentoxide, calcined sodium sulfate, concentrated sulfuric acid or calcium chloride, preferably phosphorus pentoxide.

The dehydration process can be carried out in the technical equipment customarily used for this, such as, for example, desiccators, drying pistols or drying ovens, it also being possible for a protective gas, such as, for example, nitrogen, to be used instead of air.

The dehydration process can be carried out under normal pressure or under reduced pressure, for example under waterpump vacuum. The process is speeded up when carried out in vacuo.

The dehydration is generally carried out at room temperature, but can also take place without problems at lower (for example 10° C.) or higher (for example 40° C.) temperatures.

The dehydration time depends, in particular, on the particle size of the starting material, the thickness of the layer in the equipment used and the dehydration conditions, such as, for example, the temperature and pressure. The drying time can thus vary, for example, between several hours and days.

The improved stability of the new crystalline modification compared with ceftazidim pentahydrate emerges on storage of the samples under heat stress. For example, 0.5 g of each substance is fused into a brown glass vial, stored at 80° C. for one week and then assays are carried out using, for example, high pressure liquid chromatography (HPLC). As is clear from Table 2, ceftazidim pentahydrate is virtually completely decomposed within one week while the crystalline modification according to the invention still shows an unexpectedly high stability and is thus particularly suited for medical use.

The compound according to the invention is a valuable antibiotic which is suited for controlling Gram-positive and, in particular, Gram-negative infections (cf. German Offenlegungsschrift No. 2,921,316).

Thus the invention also relates to pharmaceutical formulations which contain the compound according to the invention, such as, for example, solutions, suspensions or emulsions in oily or aqueous vehicles.

The compound according to the invention can be used as such or combined with auxiliaries customarily employed in therapy, such as, for example, formulating agents, solvents, suspending agents and/or dispersants. It is also possible for the active compound, before being used, to be present in the formulation in the form of a powder, for example, for dissolution in, for example, sterile and pyrogen-free water. In order to prepare aqueous solutions, the active compound is advantageously dissolved by the addition of a basic auxiliary, such as, for example, sodium carbonate, sodium bicarbonate, potassium bicarbonate, potassium carbonate, lithium carbonate, calcium carbonate, magnesium carbonate, trihydroxymethylmethylamine, ethylenediamine, lysine, arginine, glucosamine, N-methylglucosamine, trihydroxymethylethylamine, diethanolamine, diethylamine, piperazine or procaine.

The formulations are prepared in a manner known per se, for example by mixing, incorporation by stirring, dissolving etc. with or in the pharmaceutical auxiliaries.

The amount present in a single dose can be, for example, between about 50 and 1,500 mg of active compound, while a daily dose can amount to about 0.5 to 6 g, preferably 1 to 3 g.

EXAMPLE 20 g of ceftazidim pentahydrate are dried in a desiccator over phosphorus pentoxide (about 500 g) at room temperature (20°–25° C.), and the water lost is determined by weighing the material daily. After 12 days (decrease 2.85 g), the weight of the sample remains constant. 17.15 g of colorless crystalline ceftazidim is obtained in an anhydrous form.

The drying process is speeded up by a higher temperature (up to 50° C.) and vacuum. The NMR spectrum of anhydrous ceftazidim in $CF_3CO_2D$ completely corresponds to that of the pentahydrate in respect of the C—H proton shifts. The typical absorptions in the Debye-Scherrer diagram are shown in Table 1.

|  | $C_{22}H_{22}N_6O_7S_2$ (546.6) | | | |
| --- | --- | --- | --- | --- |
|  | C | H | N | S |
| calculated | 48.34 | 4.06 | 15.38 | 11.73 |
| found | 47.8 | 4.2 | 15.3 | 11.7 |

TABLE 1

Characteristic crystal diffraction angles of the anhydrous crystalline form of ceftazidim

| Diffraction angle $o_2\theta$ (Cu—K$_\alpha$) | d [A°] | rel. int. [%] |
|---|---|---|
| 6,75 | 13,1 | 20 |
| 9,0 | 9,82 | 100 |
| 9,15 | 9,65 | 50 |
| 10.94 | 8,08 | 15 |
| 11,50 | 7,69 | 35 |
| 11,85 | 7,47 | 10 |
| 12,65 | 7,0 | 60 |
| 13,05 | 6,77 | 20 |
| 14,30 | 6,19 | 15 |
| 16,40 | 5,40 | 20 |
| 16,95 | 5,23 | 30 |
| 17,45 | 5,08 | 10 |
| 18,80 | 4,72 | 20 |
| 19,50 | 4,55 | 60 |
| 20,45 | 4,34 | 40 |
| 21,0 | 4,23 | 40 |
| 21,95 | 4,05 | 45 |
| 24,05 | 3,70 | 10 |
| 24,65 | 3,61 | 10 |
| 25,30 | 3,52 | 20 |
| 27,05 | 3,29 | 15 |
| 28,45 | 3,14 | 10 |
| 30,90 | 2,89 | 10 |

TABLE 2

Thermal stability of ceftazidim pentahydrate (A) and anhydrous crystalline ceftazidim (B) at 80° C.

| Ceftazidim crystalline modification | Content in the samples by HPLC | | |
|---|---|---|---|
| | 0 days | 8 days | 15 days |
| A | 100% | 0% | 0% |
| B | 100% | 84.2% | 77.5% |

I claim:

1. Anhydrous crystalline (6R,7R)-7-[(Z)-2-(2-aminothiazol-4-yl)-2-(2-carboxyprop-2-oximino)acetamido]-3-(1-pyridiniummethyl)-3-cephem-4-carboxylate.

2. Pharmaceutical formulations active against bacterial infections comprising crystalline anhydrous 6R,7R)-7-[(Z)-2-(2-aminothiazol-4-yl)-2-(2-carboxyprop-2-oximino)-acetamido]-3-(1-pyridiniummethyl)-3-cephem-4-carboxylate and auxiliaries customarily used in pharmaceutical formulations.

3. A method of controlling bacterial infections comprising administering anhydrous crystalline (6R,7R)-7-[(Z)-2-(2-aminothiazol-4-yl)-2-(2-carboxyprop-2-oximino)-acetamido]-3-(1-pyridiniummethyl)-3-cephem-4-carboxylate in an amount effective to control bacterial infections.

* * * * *